United States Patent
Durschang et al.

(10) Patent No.: US 9,730,863 B2
(45) Date of Patent: *Aug. 15, 2017

(54) DENTAL RESTORATION, METHOD FOR ITS PRODUCTION AND INGOT

(75) Inventors: Bernhard Durschang, Rottendorf (DE); Jörn Probst, Kürnach (DE); Norbert Thiel, Bad Säckingen (DE); Michael Gödiker, Bad Säckingen (DE); Markus Vollmann, Gelnhausen (DE); Udo Schusser, Alzenau (DE); Michael Hackner, Bad Homburg (DE)

(73) Assignees: Fraunhofer-Gesellschaft zur förderung der angewandten Forschung e.V., München (DE); Vita Zahnfabrik H. Rauter GmbH & Co. KG, Bad Sackingen (DE); DeguDent GmbH, Hanau (DE)

( * ) Notice: Subject to any disclaimer, the term of this patent is extended or adjusted under 35 U.S.C. 154(b) by 102 days.

This patent is subject to a terminal disclaimer.

(21) Appl. No.: 14/127,040

(22) PCT Filed: Jun. 21, 2012

(86) PCT No.: PCT/EP2012/061971
§ 371 (c)(1),
(2), (4) Date: Apr. 17, 2014

(87) PCT Pub. No.: WO2012/175615
PCT Pub. Date: Dec. 27, 2012

(65) Prior Publication Data
US 2014/0252272 A1    Sep. 11, 2014

Related U.S. Application Data

(60) Provisional application No. 61/499,843, filed on Jun. 22, 2011.

(30) Foreign Application Priority Data

Jun. 22, 2011   (EP) .................................. 11005104

(51) Int. Cl.
| | | |
|---|---|---|
| *A61K 6/027* | (2006.01) | |
| *C03C 10/00* | (2006.01) | |
| *A61K 6/04* | (2006.01) | |
| *C03B 32/02* | (2006.01) | |
| *C03C 3/097* | (2006.01) | |
| *C03C 4/00* | (2006.01) | |
| *A61K 6/00* | (2006.01) | |
| *A61K 6/02* | (2006.01) | |

(52) U.S. Cl.
CPC ............ *A61K 6/043* (2013.01); *A61K 6/0094* (2013.01); *A61K 6/024* (2013.01); *A61K 6/025* (2013.01); *A61K 6/0215* (2013.01); *A61K 6/0235* (2013.01); *A61K 6/0245* (2013.01); *A61K 6/0273* (2013.01); *A61K 6/0276* (2013.01); *A61K 6/04* (2013.01); *C03B 32/02* (2013.01); *C03C 3/097* (2013.01); *C03C 4/0021* (2013.01); *C03C 10/0027* (2013.01)

(58) Field of Classification Search
CPC ..... C03B 32/02; C03C 10/0027; C03C 3/095; C03C 3/097; C03C 1/04; C03C 4/0021; A61K 6/0273
See application file for complete search history.

(56) References Cited

U.S. PATENT DOCUMENTS

| | | | |
|---|---|---|---|
| 2,684,911 A | 7/1954 | Stookey | |
| 3,238,085 A | 3/1966 | Hayami et al. | |
| 4,515,634 A | 5/1985 | Wu et al. | |
| 5,507,981 A | 4/1996 | Petticrew | |
| 5,698,482 A | 12/1997 | Frank et al. | |
| 5,925,180 A | 7/1999 | Frank et al. | |
| 7,166,548 B2 | 1/2007 | Apel et al. | |
| 7,452,836 B2 | 11/2008 | Apel et al. | |
| 7,867,930 B2 | 1/2011 | Apel et al. | |
| 7,867,931 B2 | 1/2011 | Apel et al. | |
| 7,867,933 B2 | 1/2011 | Apel et al. | |
| 7,871,948 B2 | 1/2011 | Apel et al. | |
| 7,993,137 B2 | 8/2011 | Apel et al. | |
| 8,162,664 B2 | 4/2012 | Apel et al. | |
| 8,536,078 B2 * | 9/2013 | Ritzberger ........... | A61K 6/0215 427/2.27 |
| 8,546,280 B2 | 10/2013 | Apel et al. | |
| 8,557,150 B2 | 10/2013 | Ritzberger et al. | |
| 8,759,237 B2 | 6/2014 | Ritzberger et al. | |
| 8,778,075 B2 | 7/2014 | Ritzberger et al. | |
| 8,956,987 B2 * | 2/2015 | Durschang ............. | A61K 6/024 106/35 |

(Continued)

FOREIGN PATENT DOCUMENTS

| | | |
|---|---|---|
| CA | 2213390 A1 | 3/1998 |
| CA | 2252660 A1 | 5/1999 |
| DE | 24 51 121 A1 | 5/1975 |
| DE | 10 2004 013455 B3 | 9/2005 |
| DE | 10 2005 028637 A1 | 12/2006 |
| DE | 102010050275 A1 | 5/2012 |
| EP | 0 536 572 A1 | 4/1993 |
| EP | 0 536 479 B1 | 9/1995 |
| EP | 0 690 031 A1 | 1/1996 |
| EP | 0 827 941 A1 | 3/1998 |

(Continued)

OTHER PUBLICATIONS

Borom et al., "Strength and Microstructure in Lithium Disilicate Glass-Ceramics", *Journal of The American Ceramic Society*, vol. 58, No. 9-10, pp. 385-391 (1975).

(Continued)

*Primary Examiner* — Carol M Koslow
(74) *Attorney, Agent, or Firm* — Leydig, Voit & Mayer, Ltd.

(57) ABSTRACT

The invention refers to a method for producing a dental restoration comprising a lithium silicate glass or glass ceramic as well as a dental restoration inself. The invention further refers to a ingot with the same composition having a defined strength.

12 Claims, 3 Drawing Sheets

(56) References Cited

U.S. PATENT DOCUMENTS

| | | | |
|---|---|---|---|
| 9,125,812 B2* | 9/2015 | Durschang | C03C 3/097 |
| 9,206,077 B2* | 12/2015 | Durschang | C03B 32/02 |
| 2002/0010063 A1* | 1/2002 | Schweiger | C03C 4/0021 |
| | | | 501/5 |
| 2005/0209082 A1 | 9/2005 | Apel et al. | |
| 2007/0042889 A1 | 2/2007 | Apel et al. | |
| 2009/0038344 A1 | 2/2009 | Apel et al. | |
| 2009/0038508 A1 | 2/2009 | Apel et al. | |
| 2009/0042713 A1 | 2/2009 | Apel et al. | |
| 2009/0042714 A1 | 2/2009 | Apel et al. | |
| 2010/0083706 A1 | 4/2010 | Castillo | |
| 2011/0009254 A1 | 1/2011 | Schweiger et al. | |
| 2011/0030423 A1 | 2/2011 | Johannes et al. | |
| 2011/0059836 A1 | 3/2011 | Apel et al. | |
| 2011/0252831 A1 | 10/2011 | Apel et al. | |
| 2011/0256409 A1 | 10/2011 | Ritzberger et al. | |
| 2011/0257000 A1* | 10/2011 | Ritzberger | A61K 6/0215 |
| | | | 501/32 |
| 2011/0259053 A1 | 10/2011 | Apel et al. | |
| 2012/0248642 A1 | 10/2012 | Ritzberger et al. | |
| 2012/0309607 A1 | 12/2012 | Durschang et al. | |
| 2013/0295523 A1 | 11/2013 | Durschang et al. | |
| 2013/0296156 A1 | 11/2013 | Apel et al. | |
| 2013/0323404 A1 | 12/2013 | Ritzberger et al. | |
| 2014/0000314 A1 | 1/2014 | Ritzberger et al. | |
| 2014/0249016 A1 | 9/2014 | Durschang et al. | |
| 2014/0252272 A1 | 9/2014 | Durschang et al. | |
| 2014/0335473 A1 | 11/2014 | Ritzberger et al. | |

FOREIGN PATENT DOCUMENTS

| | | |
|---|---|---|
| EP | 0 916 625 A1 | 5/1999 |
| EP | 1 505 041 A1 | 2/2005 |
| EP | 1 688 397 A1 | 8/2006 |
| EP | 2 305 614 A2 | 4/2011 |
| EP | 2 377 831 A1 | 10/2011 |
| FR | 2 655 264 A2 | 6/1991 |
| JP | H08-040744 A | 2/1996 |
| JP | H10-101409 A | 4/1998 |
| JP | H11-217239 A | 8/1999 |
| JP | H11-314938 A | 11/1999 |
| JP | 2005-053776 A | 3/2005 |
| JP | 2006-219367 A | 8/2006 |
| JP | 2007-190087 A | 8/2007 |
| JP | 2011-225441 A | 11/2011 |
| JP | 2013-515659 A | 5/2013 |
| SU | 908 355 A1 | 2/1982 |
| WO | WO 95/32678 A2 | 12/1995 |
| WO | WO 2009/126317 A1 | 10/2009 |
| WO | WO 2011/076422 A1 | 6/2011 |
| WO | WO 2012/059143 A1 | 5/2012 |
| WO | WO 2012/175450 A1 | 12/2012 |

OTHER PUBLICATIONS

De Oliveira et al., "Sintering and Crystallization of a Glass Powder in the $Li_2O$—$ZrO_2$—$SiO_2$ System," *Communications of The American Ceramic Society*, vol. 81, No. 3, pp. 777-780 (1998).

Montedo et al. "Low Thermal Expansion Sintered LZSA Glass-Ceramics," *American Ceramic Society Bulletin*, vol. 87. No. 7, pp. 34-40 (2008).

Stookey, "Chemical Machining of Photosensitive Glass", *Industrial and Engineering Chemistry*, 45, pp. 115-118 (1993).

Von Clausbruch et al., "Crystallization, Microstructure and Properties of Selected Glasses and Glass-Ceramics in the $SiO_2$—$Li_2O$—$ZnO$—$K_2O$—$P_2O_5$ System," *DGG Journal*, vol. 1, No. 1, pp. 41-49 (2002).

European Patent Office, International Search Report in International Application No. PCT/EP2012/061971 (Nov. 15, 2012).

Apel et al., "Influence of $ZrO_2$ on the crystallization and properties of lithium disilicate glass-ceramics derived from a multi-component system", *Journal of the European Ceramic Society*, 27(2-3): 1571-1577 (2007), Abstract only.

Hoeland et al., "Glass development and controlled crystallization in the $SiO_2$—$Li_2O$—$ZrO_2$—$P_2O_5$ system", *Glastech. Ber. Glass. ScL Technol.*, 69(2), (1996), Abstract only.

Intellectual Property Office of Australia, Examination Report issued in Australian Application No. 2012274050 (dated Jun. 27, 2016) 3 pp.

State Intellectual Property Office of People's Republic of China, First Office Action issued in Chinese Application No. 201280036410.0 (dated Apr. 2, 2015) 14 pp.

State Intellectual Property Office of People's Republic of China, Second Office Action issued in Chinese Application No. 201280036410.0 (dated Nov. 24, 2015) 33 pp.

State Intellectual Property Office of People's Republic of China, Decision of Rejection issued in Chinese Application No. 201280036410.0 (dated Sep. 20, 2016) 6 pp.

State Intellectual Property Office of People's Republic of China, Notification of Reexamination issued in Chinese Application No. 201280036410.0 (dated May 5, 2017) 14 pp.

European Patent Office, Office Action issued in European Application No. 12745412.2 (dated Apr. 13, 2015) 10.

Japanese Patent Office, Notice of Rejection issued in Japanese Application No. 2014-516350 (dated Apr. 12, 2016) 15 pp.

Russian Agency for Industrial Property, Patents, and Trade Marks, First Office Action issued in Russian Application No. 2013152228 (dated Jun. 24, 2016) 13 pp.

Russian Agency for Industrial Property, Patents, and Trade Marks, Second Office Action issued in Russian Application No. 2013152228 (dated Dec. 16, 2016) 12 pp.

\* cited by examiner

DENTAL RESTORATION, METHOD FOR ITS PRODUCTION AND INGOT

CROSS-REFERENCE TO RELATED APPLICATIONS

This patent application is the U.S. national phase of International Application No. PCT/EP2012/061971, filed on Jun. 21, 2012, which claims the benefit of European Patent Application No. 11005104.1 and U.S. Provisional Application No. 61/499,843, both filed Jun. 22, 2011, the disclosures of which are incorporated by reference.

The invention refers to a method for producing a dental restoration comprising a lithium silicate glass or glass ceramic as well as a dental restoration itself. The invention further refers to a ingot with the same composition having a defined strength.

In the lithium oxide-silicon dioxide system, lithium disilicate ($Li_2O.2SiO_2$ ($Li_2Si_2O_5$))-glass ceramics are well known from the literature and several patents are based on this glass ceramic system. In EP 0 536 479 B1, self-glazed lithium disilicate glass ceramic objects are thus described for the production of tableware and, in EP 0 536 572 B1, lithium disilicate glass ceramics which can be used by scattering a fine-particle coloured glass onto the surface thereof as cladding elements for building purposes, A main focus of the publications about lithium disilicate glass ceramics resides in dental applications. The lithium disilicate system is very suitable here for the production of CAD/CAM-processible glass ceramics since the crystallisation is effected here via the lithium metasilicate phase (see S. D. Stookey: "Chemical Machining of Photosensitive Glass", Ind. Eng. Chem., 45, 115-118 (1993) and S. D. Stookey: "Photosensitively Opacifiable Glass" U.S. Pat. No. 2,684,911 (1954)).

These lithium metasilicate glass ceramics have such low strengths in this intermediate stage that they can be readily processed by means of CAD/CAM (M.-P. Borom, A. M. Turkalo, R. H. Doremus: "Strength and Microstructure in Lithium Disilicate Glass Ceramics", J. Am. Ceram. Soc., 58, No. 9-10, 385-391 (1975) and DE 24 51 121 A1.

This principle is exploited in order to produce firstly a glass ceramic, in a two-stage crystallisation process, which glass ceramic can be readily processed mechanically, e.g. by means of CAD/CAM processes, and in order to process this subsequently in a second crystallisation stage to form dental glass ceramic. This method is suitable in order to be able to use dental restorations according to the so-called chair-side method. In this method, an individually adapted crown/onlay/inlay is milled out of a glass ceramic block after the first crystallisation stage by means of CAD/CAM, in the dental practice this is subjected to the second crystallisation stage in a special oven and used directly in the first and only dentist's visit for the patient (DE 10 2005 028 637).

In a first step, a glass ceramic is produced which is machineable with CAM. After the glass ceramic is machined, it is finally crystallized resulting in a material of high strength. The pre-crystallisation to a glass ceramic which is CAM-machineable is necessary due to three reasons.

At first, the starting glasses are not directly CAM-machineable since in the homogeneous amorphous system, flaking and disruptions can occur due to fracture broadening. Secondly, the final crystallisation has to be effected in a very short period which can only be guaranteed by a pre-crystallisation. Thirdly, by using glasses, the necessary conture accuracy during the final crystallisation cannot be achieved.

Starting herefrom, it was the object of the present invention to provide glass ceramics which have improved strength values and also improved translucence and chemical resistance.

This object is achieved by the method for producing a dental restoration described herein, the ingot and the dental restoration also described herein, and the advantageous developments thereof.

Within the scope of the present invention, glass compositions were developed in the basic system $SiO_2$—$Li_2O$—$ZrO_2$, which have lithium metasilicate as only or as main crystal phase (>50%).

It was surprisingly found that the use of specific lithium metasilicate compositions allows the direct machining with common CAD/CAM systems without any flakings and disruptions. Moreover, these glasses can be transformed within an extreme short period of time to glass ceramics with a very high strength. A further advantage is that the inventive glass ceramics have a very good contour accuracy.

According to the invention, a complete time- and cost-consuming process step can be saved during the production of a dental restoration without having any unwanted impact on the further properties of the materials.

The inventive method does not need an oven, thus purchasing and maintenance costs can be reduced. Furthermore, the process time can be reduced by up to 2 hours.

A further advantage of the present invention refers to the fact that dental restorations cannot only be produced by CAM but also by pressing or casting of green bodies into moldings. The inventive process allows to directly press the glass without a previous heat treatment which is used in the prior art. Moreover, it is not necessary to modify the composition to be usable for the different methods for producing the dental restorations.

High translucence is ensured via the low crystallite size in the glass ceramics.

In addition, good chemical stability is ensured by the high zirconium oxide proportion in the glass phase.

According to the present invention, a method for producing a dental restoration comprising a lithium silicate glass ceramic is provided having the following steps:
a) an amorphous glass with the composition
   50 to 70 wt-% $SiO_2$,
   10 to 25 wt-% $Li_2O$,
   8 to 20 wt-% of a stabilizer selected from the group consisting of oxides of Zr, Hf, Ge, La, Y, Ce, Ti, Zn, or its mixtures,
   0 to 10 wt-% $Al_2O_3$,
   0 to 10 wt-% $K_2O$ and/or $Na_2O$, and
   0 to 20 wt-% additives
   is provided as an ingot,
b) the ingot is transformed to a dental restoration by at least one transformation process, wherein during the at least one transformation process at least a partial crystallisation occurs due to increased temperatures.

The increased temperature is at least 50° C., preferably at least 300° C. above the transformation temperature of the glass, i.e. in general at least 800° C.

In a preferred embodiment, the amorphous glass has the following composition:
   50 to 70 wt-% $SiO_2$,
   10 to 25 wt-% $Li_2O$,
   8 to 20 wt-% of a stabilizer from a group selected of $ZrO_2$, $HfO_2$ or its mixtures,
   0 to 10 wt-% $Al_2O_3$,
   0 to 10 wt-% $K_2O$ and/or $Na_2O$, and
   0 to 20 wt-% additives.

In a further preferred embodiment, the amorphous glass has the following composition:
- 55 to 64 wt-% $SiO_2$,
- 15 to 22 wt-% $Li_2O$,
- 8 to 20 wt-% of a stabilizer from a group selected of $ZrO_2$, $HfO_2$ or its mixtures,
- 0.1 to 8 wt-% $Al_2O_3$,
- 0 to 8 wt-% $K_2O$ and/or $Na_2O$, and
- 0 to 10 wt-% additives.

More preferably, the amorphous glass has the following composition:
- 55 to 64 wt-% $SiO_2$,
- 17 to 20 wt-% $Li_2O$,
- 8 to 20 wt-% of a stabilizer from a group selected of $ZrO_2$, $HfO_2$ or its mixtures,
- 0.1 to 5 wt-% $Al_2O_3$,
- 0.1 to 5 wt-% $K_2O$ and/or $Na_2O$,
- 2 to 8 wt-% $P_2O_5$, and
- 0 to 10 wt-% additives.

In accordance with an embodiment, the amorphous glass has the following composition:
- 55 to 64 wt-% $SiO_2$,
- 15 to 22 wt-%, preferably 17 to 20 wt-% of $Li_2O$,
- 8 to 20 wt-%, preferably 10 to 15 wt-% of a stabilizer selected from a group selected of $ZrO_2$, $HfO_2$ and mixtures thereof,
- 0 to 10 wt-%, preferably 0.1 to 8 wt-% and more preferably 1 to 5 wt-% of $Al_2O_3$,
- 0 to 10 wt-%, preferably 0.1 to 5 wt-% of $K_2O$ and/or $Na_2O$,
- 0 to 8 wt-% $P_2O_5$, and
- 0 to 20 wt-%, preferably 0.1 to 10 wt-% of additives.

In an embodiment, the amorphous glass has the following composition:
- 55 to 64 wt-% $SiO_2$,
- 17 to 20 wt-% of $Li_2O$,
- 10 to 15 wt-% of a stabilizer selected from $ZrO_2$, $HfO_2$ and mixtures thereof,
- 0.1 to 8 wt-% of $Al_2O_3$,
- 0.1 to 5 wt-% of $K_2O$ and/or $Na_2O$,
- 0 to 8 wt-% $P_2O_5$, and
- 0.1 to 10 wt-% of additives.

Preferably, during the transformation process, thermal energy is conveyed to the ingot, preferably by heating the ingot to temperatures between 850° C. and 1100° C. This heat treatment is preferably performed over a period from 10 to 120 minutes.

In an embodiment of the method, during the transformation process, thermal energy is conveyed to the ingot, preferably with temperatures of at least 800° C., more preferably with temperatures from 850° C. to 1100° C., preferably performed over a period from 10 to 120 min.

It is preferred that in a further step c) subsequent to the transformation process, the dental restoration is subjected to a second heat treatment with temperatures from 850° C. to 1100° C.

The stabilizer is preferably $ZrO_2$ and/or $HfO_2$. Preferably, the stabilizer is essentially present in an amorphous state.

There may be contained as additives components selected from the group consisting of nucleation agents, fluorescent agents, dyes, in particular glass-colouring oxides, coloured pigments and mixtures thereof, in the glass or in the glass ceramic.

The nucleating agents are preferably selected from the group consisting of phosphorous oxide, titanium oxide, tin oxide, mixtures thereof, and noble metals, preferably in an amount of 1 to 10 wt-%, more preferably 2 to 8 wt-% and most preferably 4 to 8 wt-%.

In an embodiment, the fluorescent agents are selected from the group consisting of oxides of strontium, bismuth, rare earth elements neodymium, praseodymium, samarium, europium, terbium, dysprosium, holmium, erbium, and mixtures thereof, preferably in an amount of 0.1 to 5 wt-%, more preferably 0.5 to 4 wt-% and most preferably 1 to 3 wt-%.

The fluorescent agents are preferably selected from the group consisting of oxides of strontium, bismuth, rare earth elements as neodymium, praseodymium, samarium, erbium, and europium, and mixtures thereof, preferably in an amount of 0.1 to 5 wt-%, more preferably 0.5 to 4 wt-% and most preferably 1 to 3 wt-%.

The glass colouring oxides are preferably selected from the group of oxides of iron, titanium, cerium, copper, chromium, cobalt, nickel, manganese, selenium, silver, indium, gold, vanadium, rare earth elements as neodymium, praseodymium, samarium, europium, terbium, dysprosium, holmium, erbium, yttrium, and mixtures thereof, preferably in an amount of 0.1 to 6 wt-%, more preferably 0.5 to 5 wt-% and most preferably 1 to 4 wt-%.

The coloured pigments can be doped spinels, which are comprised preferably in an amount of 0.1 to 6 wt-%, more preferably 0.5 to 5 wt-% and most preferably 1 to 4 wt-%.

Further additives are preferably selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, which are comprised preferably in an amount of 0.1 to 5 wt-%.

The transformation process is preferably a lost wax process, e.g. a moulding, a casting, a pressing or combinations thereof.

In a further preferred embodiment, the dental restoration is subjected to a finishing process before the dental application. Such a finishing process can be a polishing, a glazing, a sealing, a coating, and a veneering with a veneering ceramic or glaze.

The dental restoration is preferably an inlay, an onlay, a bridge, an abutment, a facing, a veneer, a facet, a crown, a partial crown, a framework or a coping.

According to the present invention, also a ingot, i.e. a press pellet, with the following composition is provided:
- 55 to 70 wt-% $SiO_2$,
- 10 to 25 wt-% $Li_2O$,
- 8 to 20 wt-% of a stabilizer selected from the group consisting of the oxides of Zr, Hf, Ge, La, Y, Ce, Ti, Zn or its mixtures,
- 0 to 10 wt-% $Al_2O_3$,
- 0 to 10 wt-% $K_2O$ and/or $Na_2O$, and
- 0 to 20 wt-% additives.

Preferably, the ingot has the following composition:
- 50 to 70 wt-% $SiO_2$,
- 10 to 25 wt-% $Li_2O$,
- 8 to 20 wt-% of a stabilizer from a group selected of $ZrO_2$, $HfO_2$ or its mixtures,
- 0 to 10 wt-% $Al_2O_3$,
- 0 to 10 wt-% $K_2O$ and/or $Na_2O$, and
- 0 to 20 wt-% additives.

In an embodiment, the ingot has the following composition:
- 55 to 64 wt-% $SiO_2$,
- 15 to 22 wt-%, preferably 17 to 20 wt-% of $Li_2O$, 8 to 20 wt-%, preferably 10 to 15 wt-% of a stabilizer selected from a group selected of $ZrO_2$, $HfO_2$ and mixtures thereof,
0 to 10 wt-%, preferably 0.1 to 8 wt-% and more preferably 1 to 5 wt-% of $Al_2O_3$,
0 to 10 wt-%, preferably 0.1 to 5 wt-% of $K_2O$ and/or $Na_2O$,
0 to 8 wt-% $P_2O_5$, and
0 to 20 wt-%, preferably 0.1 to 10 wt-% of additives.

More preferably, the ingot has the following composition:
55 to 64 wt-% $SiO_2$,
15 to 22 wt-% $Li_2O$,
8 to 20 wt-% of a stabilizer from a group selected of $ZrO_2$, $HfO_2$ or its mixtures,
0.1 to 8 wt-% $Al_2O_3$,
0 to 8 wt-% $K_2O$ and/or $Na_2O$, and
0 to 10 wt-% additives.

In a further preferred embodiment, the ingot has the following composition:
55 to 64 wt-% $SiO_2$,
17 to 20 wt-% $Li_2O$,
8 to 20 wt-% of a stabilizer from a group selected of $ZrO_2$, $HfO_2$ or its mixtures,
0.1 to 5 wt-% $Al_2O_3$,
0.1 to 5 wt-% $K_2O$ and/or $Na_2O$,
2 to 8 wt-% $P_2O_5$, and
0 to 10 wt-% additives.

According to the present invention, furthermore, a dental restoration is provided which is producible by the above described method.

It is preferred that the dental restoration has a degree of crystallization of at least 5%, preferably at least 50%.

It is further preferred that the dental restoration has a strength of at least 200 MPa, preferably 250 MPa (measured according to DIN ISO 6872).

The dental restoration can have a finishing. Such a finishing is preferably a polishing, a glazing, a sealing, a coating, and a veneering with a veneering ceramic or glaze. Such a finished dental restoration has preferably a strength of at least 250 MPa, preferably 300 MPa (measured according to DIN ISO 6872).

The dental restorations with the following compositions are further aspects of the present invention:

| Composition 1 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 2 | |
|---|---|
| $SiO_2$ | 50 to 64 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 3 | |
|---|---|
| $SiO_2$ | 55 to 60 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 4 | |
|---|---|
| $SiO_2$ | 50 to 75 wt-% |
| $Li_2O$ | 15 to 22 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 5 | |
|---|---|
| $SiO_2$ | 50 to 75 wt-% |
| $Li_2O$ | 17 to 20 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 6 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 7 | |
|---|---|
| $SiO_2$ | 50 to 75 wt-% |
| $Li_2O$ | 10 to 25 wt-% |
| $ZrO_2$ | 10 to 15 wt-% |
| $Al_2O_3$ | 0 to 8 wt-% |
| $K_2O$ | 0 to 8 wt-% |
| additives | 0 to 15 wt-% |

| Composition 8 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0.1 to 5 wt-% |
| $K_2O$ | 0 to 8 wt-% |
| additives | 0 to 15 wt-% |

| Composition 9 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 1 to 3 wt-% |
| $K_2O$ | 0 to 8 wt-% |
| additives | 0 to 15 wt-% |

| Composition 10 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0.1 to 5 wt-% |
| additives | 0 to 15 wt-% |

| Composition 11 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 1 to 3 wt-% |
| additives | 0 to 15 wt-% |

| Composition 12 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 1 to 10 wt-% |

| Composition 13 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |

-continued

| | |
|---|---|
| K₂O | 0 to 8 wt-% |
| additives | 2 to 8 wt-% |

Composition 14

| | |
|---|---|
| SiO₂ | 50 to 75 wt-% |
| Li₂O | 10 to 25 wt-% |
| ZrO₂ | 8 to 20 wt-% |
| Al₂O₃ | 0 to 8 wt-% |
| K₂O | 0 to 8 wt-% |
| additives | 4 to 6 wt-% |

Composition 15

| | |
|---|---|
| SiO₂ | 50 to 75 wt-% |
| Li₂O | 10 to 25 wt-% |
| ZrO₂ | 8 to 20 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 16

| | |
|---|---|
| SiO₂ | 50 to 75 wt-% |
| Li₂O | 10 to 25 wt-% |
| ZrO₂ | 8 to 20 wt-% |
| P₂O₅ | 2 to 8 wt-% |
| Al₂O₃ | 0 to 8 wt-% |
| K₂O | 0 to 8 wt-% |
| additives | 0 to 7 wt-% |

Composition 17

| | |
|---|---|
| SiO₂ | 50 to 75 wt-% |
| Li₂O | 10 to 25 wt-% |
| ZrO₂ | 8 to 20 wt-% |
| P₂O₅ | 4 to 6 wt-% |
| Al₂O₃ | 0 to 8 wt-% |
| K₂O | 0 to 8 wt-% |
| additives | 0 to 9 wt-% |

Composition 18

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 19

| | |
|---|---|
| SiO₂ | 55 to 64 wt-% |
| Li₂O | 15 to 22 wt-% |
| ZrO₂ | 8 to 20 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 20

| | |
|---|---|
| SiO₂ | 55 to 64 wt-% |
| Li₂O | 17 to 20 wt-% |
| ZrO₂ | 8 to 20 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 21

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 22

| | |
|---|---|
| SiO₂ | 55 to 64 wt-% |
| Li₂O | 10 to 25 wt-% |
| ZrO₂ | 8 to 15 wt-% |
| P₂O₅ | 1 to 10 wt-% |
| Al₂O₃ | 0 to 8 wt-% |
| K₂O | 0 to 8 wt-% |
| additives | 0 to 5 wt-% |

Composition 23

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 0.1 to 5 wt-% |
| K₂O | 0 to 8 wt-% |
| additives | 0 to 5 wt-% |

Composition 24

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 1 to 3 wt-% |
| K₂O | 0 to 8 wt-% |
| additives | 0 to 5 wt-% |

Composition 25

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 0 to 8 wt-% |
| K₂O | 0.1 to 5 wt-% |
| additives | 0 to 5 wt-% |

Composition 26

| | |
|---|---|
| SiO₂ | 55 to 64 wt-% |
| Li₂O | 10 to 25 wt-% |
| ZrO₂ | 8 to 20 wt-% |
| P₂O₅ | 1 to 10 wt-% |
| Al₂O₃ | 0 to 8 wt-% |
| K₂O | 1 to 3 wt-% |
| additives | 0 to 5 wt-% |

The subject according to the application is intended to be explained in more detail with reference to the subsequent figures and examples without restricting said subject to these variants.

EXAMPLE 1

Figure 1:
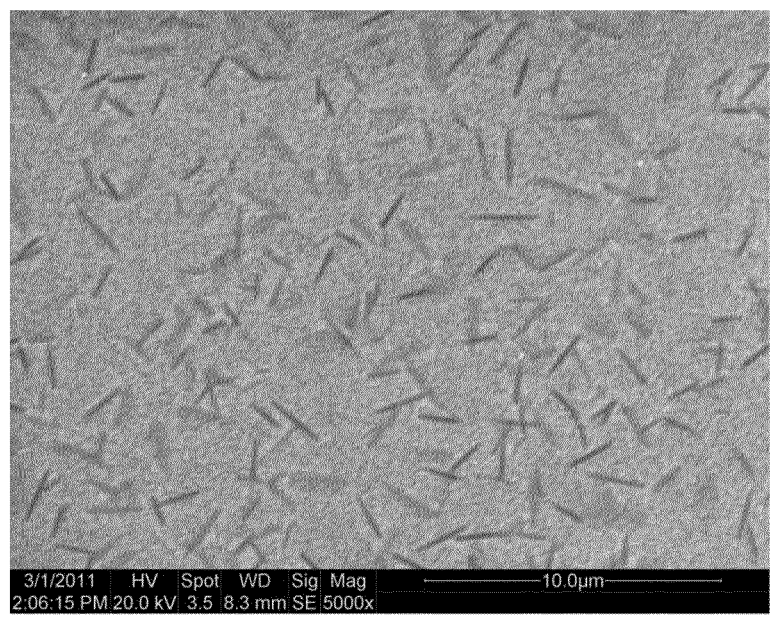
FIG. 1 shows a Scanning Electron microscope (SEM) micrograph of a glass according to the present invention after pre-crystallization.

In Table 1, a fixed compositions given by way of example for different stabilizer is mentioned, from which high stabilizer-containing metasilicate glass ceramics can be produced for the dental field.

TABLE 1

| | in % by weight |
|---|---|
| SiO₂ | 60.0 |
| Li₂O | 19.0 |
| P₂O₅ | 6.0 |
| Al₂O₃ | 2.0 |
| K₂O | 2.0 |
| CeO₂ | 1.0 |
| Stabilizer SX* | 10.0 |

*SX represent compositions of stabilizers S1 to S5 (s. table 2)

Table 2 shows stabilizers used by way of example for dental applications with the composition of table 1.

TABLE 2

| | Stabilizers SX |
|---|---|
| S1 | Zirconium oxide: 10% |
| S2 | Germanium oxide: 10% |
| S3 | Lanthanum oxide: 10% |
| S4 | Yttrium oxide: 10% |
| S5 | Zirconium oxide: 6% |
| | Titanium oxide: 4% |

The glasses were melted at 1.500° C. and poured into metal moulds to form blocks. The blocks were stress-relieved in the oven at 560° C. and cooled down slowly. For the various characterisation processes, the glass blocks were divided up and subjected to a first crystallisation treatment. For this purpose, the glasses were stored for 10 to 120 minutes at 600° C. to 750° C. As a result of this, glass ceramics with strength values of 150 MPa to 220 MPa were produced. Exclusively lithium metasilicate was hereby established as crystal phase. In this state, processing by means of CAD/CAM methods is possible very readily.

In Table 3, compositions which are given by way of example are mentioned, from which high zirconium oxide-containing metasilicate glass ceramics can be produced for the dental field.

TABLE 3

| | G1* | G2* | G3* | G4* | G5* | G6* |
|---|---|---|---|---|---|---|
| $SiO_2$ | 63.5 | 63.5 | 59.0 | 59.0 | 63.5 | 63.5 |
| $Li_2O$ | 12.9 | 13.9 | 18.0 | 19.0 | 12.9 | 12.9 |
| $ZrO_2$ | 10.0 | 9.0 | 12.0 | 12.0 | 12.3 | 11.0 |
| $Al_2O_3$ | 4.7 | 5.1 | 4.5 | 4.5 | 3.9 | 4.4 |
| $P_2O_5$ | 4.5 | 4.5 | 3.5 | 3.5 | 3.7 | 4.2 |
| $K_2O$ | 4.4 | 4.0 | 3.0 | 2.0 | 3.6 | 4.0 |

*(Data in % by weight)

The glasses were melted at 1.500° C. and poured into metal moulds to form blocks. The blocks were stress-relieved in the oven at 560° C. and cooled down slowly. For the various characterisation processes, the glass blocks were divided up and subjected to a first crystallisation treatment. For this purpose, the glasses were stored for 10 to 120 minutes at 600° C. to 750° C. As a result of this, glass ceramics with strength values of 150 MPa to 220 MPa were produced. Exclusively lithium metasilicate was hereby established as crystal phase. In this state, processing by means of CAD/CAM methods is possible very readily.

EXAMPLE 2

An inventive dental restoration was produced according to the following process steps:
1. Melting of components to homogeneous liquid glass
2. Molding of glass blanks
3. Relief of stress within glass blank
4. Optional: Pre-crystallization of glass blank (process not necessary for high strength press result)

The glass blanks are placed on firing trays, e.g. made of glass fibers. A thermal treatment 550-700° C., dwell time 10-60 min, heating rate 10-100° C./min and final temperature 800-850° C., dwell time 8-30 min in atmosphere.

The microstructure shows a poly-crystalline state with crystals <5 μm (s. FIG. 1).

XRD analysis shows phases of lithium silicate ($Li_2SiO_3$) and lithium phosphate ($Li_3PO_4$).

5. Modellation of the desired prosthesis in wax

A full anatomical wax modellation of the prosthesis will be made out of residue free burning wax. The minimal thickness of the wax modellation should not be below 0.4 mm and should not exceed 2.0 mm on occlusal side. Wax sprues will be added to the modellation with a length of 5-6 mm and a thickness of 3-4 mm.

6. Investment of the wax modellation

The investment mass will be stirred and poured bubble-free into the muffle under vibration where the wax modellation is fixed in until the wax modellation is completely covered by the investment mass. After this the muffle will be filled completely without applying vibration. The muffle with the liquid investment mass will now be stored to set the hardening process.

7. Heating of the muffle and burning off of the wax modellation

After setting of the investment mass any of the auxiliary plastic parts will be removed and the surfaces (top/bottom) will be cleaned to obtain a plane surface.

The muffle will be placed in the pre-heating furnace. The base temperature depends on the kind of used investment mass. By using the Dentsply investment mass the muffle can be placed directly after the setting of 15 min in furnace pre-heated to 850° C.

8. Pressing of the restoration

The muffle then will be cooled down for 15 min to 700° C. The starting temperature of the pressing process is 600° C. Press-pellets of TW4 with a high strength are placed in the muffle. A non heated press rod made of alumina or investment mass now setting on the press pellets. The muffle with the pellets and the press rod will be placed now immediately into the pressing furnace and a press program with the following parameters will be started: Pre-heating temperature 600-850° C., heating rate 30-100° C./min, pressing temperature 890-995° C., dwell time 10-35 min, pressing time 1-20 min. After the pressing is completed the muffle will be put out of the furnace and will be cooled down at room temperature.

Figure 2:
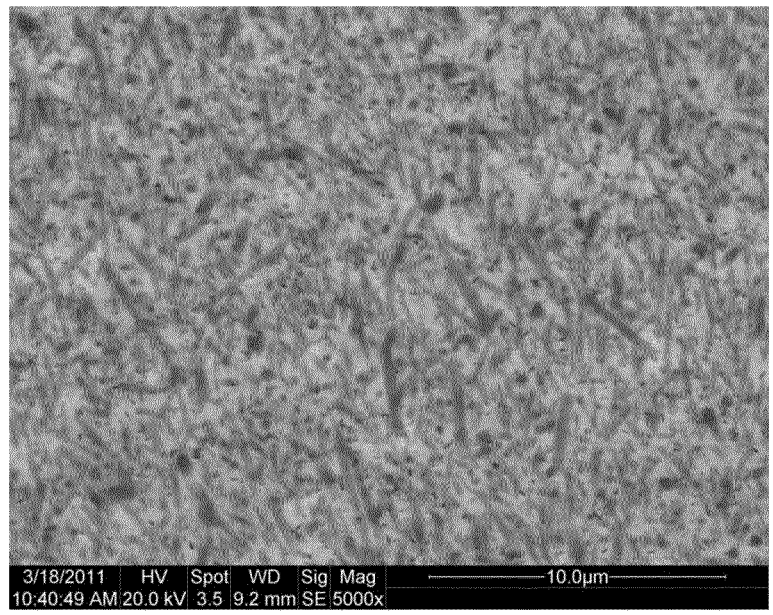
FIG. 2 shows a Scanning Electron microscope (SEM) micrograph of a glass according to the present invention after pressing at a temperature of 950° C.

After pressing the polycrystalline structure can be seen in FIG. 2.

Figure 3:
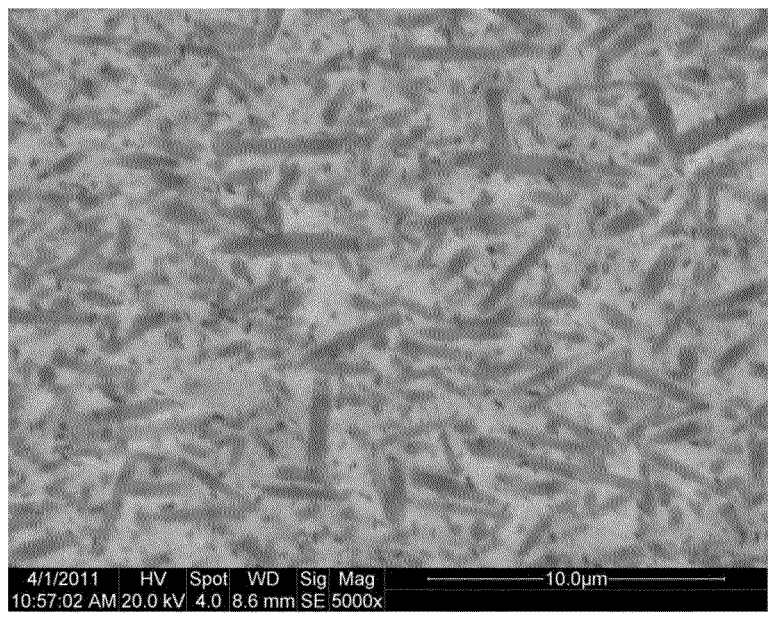
FIG. 3 shows a Scanning Electron microscope (SEM) micrograph of a glass according to the present invention after pressing at a temperature of 970° C.

Due to a variation of the pressing temperature the crystal size can be changed. Pressing temperatures of 950° C. to 970° C. resulting in crystal sizes of 1500 nm to 3000 nm (median) (s. FIG. 3).

3-point-bending tests in accordance to DIN EN ISO 6872: 2008 shows a flexural strength of 370 MPa and the coefficient of thermal expansion at 25-400° C. is 10.6-10.9 μm/mK, for 25-500° C. 11.0-11.3 μm/mK and for 25-600° C. 11.4-11.8 μm/mK.

XRD shows phases of lithium silicate ($Li_2SiO_3$) and lithium phosphate ($Li_3PO_4$). Different pressing temperatures do not show significantly different crystal phases.

9. Divesting of the pressed restoration

The investment mass will be removed by blasting with glass beads having a diameter of 50 μm with a pressure of 2-4 bar or sandblasting with alumina (diameter 110 μm, 0.5-2 bar).

10. Removing of the reaction layer of the pressed restoration

The residues of the reaction layer are removed in a ultrasonic bath with a hydrofluoric acid containing solvent for 30 min at 30° C.

11. Cutting off the sprues from the restoration

The sprue will be cut-off with a water-cooled diamond saw and cleaned. The surface to be veneered or glazed will be sandblasted with alumina having a median diameter of 110 μm and a pressure of 0.5-1.5 bar.

12. Shading with glaze/stains and veneering technique, respectively

The pressed restoration will be esthetically individualized either with glaze/stains using 2-3 firing cycles or will be finalized with veneering ceramic using the cut-back technique.

EXAMPLE 3

An inventive dental restoration was produced according to the following process steps:
1. Melting of components to homogeneous liquid glass
2. Molding of glass blanks
3. Relief of stress within glass blank
4. Optional: Pre-crystallization of glass blank (process not necessary for high strength press result)
5. Modellation of the desired prosthesis in wax.

A full anatomical wax modellation of the prosthesis will be made out of residue free burning wax. The minimal thickness of the wax modellation should not be below 0.4 mm and should not exceed 2.0 mm on occlusal side. Wax sprues will be added to the modellation with a length of 5-6 mm and a thickness of 3-4 mm.

6. Investment of the wax modellation

The investment mass (gypsum or phosphate based) will be stirred and poured bubble-free into the muffle under vibration where the wax modellation is fixed in until the wax modellation is completely covered by the investment mass. After this the muffle will be filled completely without applying vibration. The muffle with the liquid investment mass will now be stored to set the hardening process.

7. Heating of the muffle and burning off of the wax modellation.

When using a gypsum investment the maximum temperature of about 700° C. has to be taken into account.

After setting of the investment mass any of the auxiliary plastic parts will be removed and the surfaces (top/bottom) will be cleaned to obtain a plane surface.

The muffle will be placed in the pre-heating furnace. The base temperature depends on the kind of used investment mass. By using the Dentsply investment mass the muffle can be placed directly after the setting of 15 min in furnace pre-heated to 850° C.

8. Casting of the restoration

The muffle then will be cooled down for 15 min to 700° C. For casting a suitable casting machine will be used for e.g. a Prestomat from DeguDent. The blank or pellet of TW4 produced as described before will be heated up to temperature of 1150° C. and then will be casted in the already preheated muffle (700° C.). After the casting is completed the muffle will be put out of the casting device and into a pre-heating furnace at 660° for 40 min for nucleation purposes. After this either the muffle will be heated up to crystallization temperature (e.g. 850° C., 5 min.) or the muffle will be cooled down at room temperature and the final crystallization takes place after being divested.

Due to a variation of the nucleation and final crystallization temperature the crystal size can be changed. Different temperatures of nucleation of 600° C. to 850° C. and final crystallization from 750° C. to 850° C. resulting in crystal sizes of 100 nm to 3000 nm (median).

3-point-bending tests in accordance to DIN EN ISO 6872: 2008 shows a flexural strength of 370 MPa and the coefficient of thermal expansion at 25-400° C. is 10.6-10.9 μm/mK, for 25-500° C. 11.0-11.3 μm/mK and for 25-600° C. 11.4-11.8 μm/mK.

XRD shows phases of lithium silicate ($Li_2SiO_3$) and lithium phosphate ($Li_3PO_4$). Different pressing temperatures do not show significantly different crystal phases.

9. Divesting of the cast restoration

The investment mass will be removed either by blasting with glass beads having a diameter of 50 μm with a pressure of 2-4 bar or sandblasting with alumina (diameter 110 μm, 0.5-2 bar) or by using gypsum investment masses by dissolving in a water tank at room temperature.

10. Cutting off the sprues from the restoration

The sprue will be cut-off with a water-cooled diamond saw and cleaned. The surface to be veneered or glazed will be sandblasted with alumina having a median diameter of 110 μm and a pressure of 0.5-1.5 bar. An advantage of the casting is a significantly reduced reaction layer or even no reaction layer. Therefore, reproduction of fine surface details (e.g. of thin margins) is superi- or especially if gypsum investment is used (easy to remove).

11. Shading with glaze/stains and veneering technique, respectively

The pressed restoration will be esthetically individualized either with glaze/stains using 2-3 firing cycles or will be finalized with veneering ceramic using the cut-back technique.

The invention claimed is:

1. A method for producing a dental restoration comprising a lithium silicate glass ceramic, wherein
   a) an amorphous glass with the composition
      50 to 75 wt-% $SiO_2$,
      17 to 25 wt-% $Li_2O$,
      8 to 20 wt-% $HfO_2$ or of a mixture of $HfO_2$ and $ZrO_2$,
      0 to 8 wt-% $Al_2O_3$,
      0 to 8 wt-% $K_2O$, and
      0 to 15 wt-% additives
      is provided as an ingot and
   b) the ingot is transformed to a dental restoration by at least one transformation process, wherein during the at least one transformation process at least a partial crystallisation occurs due to increased temperatures,
   wherein the transformation process is a lost wax process.

2. The method of claim 1, wherein the amorphous glass has the following composition:
   55 to 64 wt-% $SiO_2$,
   17 to 22 wt-% of $Li_2O$,
   8 to 20 wt-% $HfO_2$ or of a mixture of $HfO_2$ and $ZrO_2$,
   0.1 to 5 wt-% of $Al_2O_3$,
   0.1 to 5 wt-% of $K_2O$,
   2 to 8 wt-% $P_2O_5$, and
   0 to 10 wt-% of additives.

3. The method of claim 1, wherein during the transformation process, thermal energy is conveyed to the ingot, with temperatures of at least 800° C.

4. The method of claim 1,
   wherein in a further step c) subsequent to the transformation process, the dental restoration is subjected to a heat treatment with temperatures from 850° C. to 1100° C.

5. The method of claim 1, wherein the additives are selected from nucleating agents, fluorescent agents, dyes, glass colouring oxides, coloured pigments, and mixtures thereof.

6. The method of claim 5, wherein the nucleating agents are selected from phosphorous oxide, titanium oxide, tin oxide, and mixtures thereof, and noble metals.

7. The method of claim 5, wherein the fluorescent agents are selected from oxides of strontium, bismuth, rare earth elements, and mixtures thereof.

8. The method of claim 5, wherein the glass colouring oxides are selected from oxides of iron, titanium, copper, chromium, cobalt, nickel, manganese, selenium, silver, indium, gold, vanadium, rare earth elements, and mixtures thereof.

9. The method of claim 1, wherein the additives are selected from boron oxide, fluorine, barium oxide, strontium oxide, magnesium oxide, zinc oxide, calcium oxide, yttrium oxide, titanium oxide, niobium oxide, tantalum oxide, lanthanum oxide and mixtures thereof.

10. The method of claim 1, wherein before the dental application, the dental restoration is subjected to a finishing process selected from polishing, glazing, sealing, coating, and veneering with a veneering ceramic or glaze.

11. The method of claim 6, wherein the nucleating agent is present in an amount of 1 to 10 wt-% of the dental restoration.

12. The method of claim 7, wherein the fluorescent agent is present in an amount of 0.1 to 5 wt-% of the dental restoration.

\* \* \* \* \*